(12) United States Patent  
Johnson et al.

(10) Patent No.: US 9,895,090 B2  
(45) Date of Patent: Feb. 20, 2018

(54) REGIONAL OXIMETRY SLEEVE FOR MOBILE DEVICE

(71) Applicant: Nonin Medical, Inc., Plymouth, MN (US)

(72) Inventors: Timothy L. Johnson, Plymouth, MN (US); Bryant Austin Jones, Minneapolis, MN (US); Christopher Holland, Mayer, MN (US)

(73) Assignee: Nonin Medical, Inc., Plymouth, MN (US)

( * ) Notice: Subject to any disclaimer, the term of this patent is extended or adjusted under 35 U.S.C. 154(b) by 314 days.

(21) Appl. No.: 14/082,950

(22) Filed: Nov. 18, 2013

(65) Prior Publication Data

US 2015/0141779 A1   May 21, 2015

(51) Int. Cl.
| | |
|---|---|
| *A61B 5/00* | (2006.01) |
| *A61B 5/1455* | (2006.01) |
| *A61B 5/0205* | (2006.01) |
| *A61B 5/145* | (2006.01) |

(52) U.S. Cl.
CPC ...... *A61B 5/14552* (2013.01); *A61B 5/02055* (2013.01); *A61B 5/002* (2013.01); *A61B 5/14535* (2013.01); *A61B 2560/045* (2013.01)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| 5,810,724 | A  * | 9/1998  | Gronvall ............ A61B 5/02427 600/310 |
| 6,622,034 | B1 * | 9/2003  | Gorski ............... A61B 5/14552 600/310 |
| 7,671,351 | B2 * | 3/2010  | Setlak ................ G06K 9/00013 250/208.1 |
| 8,301,232 | B2   | 10/2012 | Albert et al. |
| 2002/0082489 | A1 | 6/2002  | Casciani et al. |
| 2002/0116797 | A1* | 8/2002  | Modgil ............. A61B 5/14552 24/306 |

(Continued)

FOREIGN PATENT DOCUMENTS

WO   WO-2014159723 A2   10/2014

OTHER PUBLICATIONS

U.S. Appl. No. 13/829,158, Final Office Action dated Jan. 4, 2016, 12 pgs.

(Continued)

*Primary Examiner* — Eric Winakur
(74) *Attorney, Agent, or Firm* — Schwegman Lundberg & Woessner, P.A.

(57) ABSTRACT

A system includes a mobile computing device, a sleeve, a contact surface, a sensor module, and a telemetry module. The mobile computing device has a first processor within a housing. The sleeve has an internal surface configured to fit the housing. The contact surface is disposed on an external surface of the sleeve. The sensor module is coupled to the contact surface and is configured to generate an electrical signal corresponding to a measured physiological parameter associated with tissue at the contact surface. The telemetry module is coupled to the sensor module and is configured to communicate data corresponding to the electrical signal to the mobile computing device.

16 Claims, 3 Drawing Sheets

(56) References Cited

U.S. PATENT DOCUMENTS

| | | | |
|---|---|---|---|
| 2008/0139908 A1* | 6/2008 | Kurth | A61B 5/14553 600/340 |
| 2009/0105605 A1 | 4/2009 | Abreu | |
| 2009/0163787 A1 | 6/2009 | Mannheimer et al. | |
| 2010/0010326 A1 | 1/2010 | Dalvi et al. | |
| 2010/0125188 A1 | 5/2010 | Schilling et al. | |
| 2010/0240972 A1* | 9/2010 | Neal | A61B 5/14552 600/324 |
| 2010/0312080 A1* | 12/2010 | Isaacson | A61B 5/14552 600/323 |
| 2010/0331631 A1 | 12/2010 | Maclaughlin | |
| 2011/0077473 A1 | 3/2011 | Lisogurski | |
| 2011/0224518 A1 | 9/2011 | Tindi et al. | |
| 2012/0059267 A1 | 3/2012 | Lamego et al. | |
| 2014/0200054 A1* | 7/2014 | Fraden | H04M 1/0254 455/575.8 |
| 2014/0275885 A1 | 9/2014 | Isaacson et al. | |
| 2015/0099951 A1 | 4/2015 | Al-ali et al. | |
| 2015/0141780 A1 | 5/2015 | Meyer et al. | |

OTHER PUBLICATIONS

U.S. Appl. No. 13/829,158, Non Final Office Action dated Jul. 6, 2015, 11 pgs.

U.S. Appl. No. 13/829,158, Response filed Dec. 2, 2015 to Non Final Office Action dated Jul. 6, 2015, 12 pgs.

U.S. Appl. No. 14/082,975, Final Office Action dated Mar. 24, 2016, 20 pgs.

U.S. Appl. No. 14/082,975, Non Final Office Action dated Aug. 26, 2015, 16 pgs.

U.S. Appl. No. 14/082,975, Response filed Feb. 25, 2016 to Non Final Office Action dated Aug. 26, 2015, 21 pgs.

U.S. Appl. No. PCT/US2014/024906, International Preliminary Report on Patentability dated Sep. 24, 2015, 7 pgs.

European Application Serial No. 14775821.3, Response filed May 2, 2016 to Communication pursuant to Rules 161(2) and 162 EPC dated Oct. 22, 2015, 14 pgs.

International Application Serial No. PCT/US2014/024906, International Search Report dated Sep. 16, 2014, 2 pgs.

International Application Serial No. PCT/US2014/024906, Written Opinion dated Sep. 16, 2014, 5 pgs.

U.S. Appl. No. 13/829,158 Response filed Jan. 30, 2017 to Final Office Action dated Jul. 18, 2016, 16 pgs.

U.S. Appl. No. 13/829,158, Non Final Office Action dated Feb. 22, 2017, 12 pgs.

U.S. Appl. No. 14/082,950 Response filed Feb. 16, 2017 to Advisory Action dated Feb. 8, 2017, 16 pgs.

U.S. Appl. No. 14/082,975, Non Final Office Action dated Jul. 27, 2017, 13 pgs.

U.S. Appl. No. 14/082,975, Response filed Apr. 14, 2017 to Final Office Action dated Oct. 14, 2016, 13 pgs.

\* cited by examiner

US 9,895,090 B2

REGIONAL OXIMETRY SLEEVE FOR MOBILE DEVICE

BACKGROUND

A measure of regional oximetry can provide an indication as to tissue health. Existing technology for measuring regional oximetry is inadequate. One example includes an optical sensor coupled by a wire to a separate processing module. The sensor may be secured to the patient by an adhesive or by a strap encircling the patient and is tethered by wire to the processing module.

This arrangement of a sensor and a processor module with a connecting wire is unsatisfactory for certain applications. For example, in an emergency situation or a battlefield environment, the separate nature of the modules and the connecting wire can be inconvenient and may be prone to failure.

OVERVIEW

The present inventors have recognized, among other things, that a problem to be solved can include providing a system for measuring regional oximetry based on a rapidly established temporary coupling to the tissue and using a mobile computing device. The present subject matter can help provide a solution to this problem, such as by a system including a sensor module that can be coupled to a mobile device and manually positioned at a tissue site. The mobile device can display results and can communicate the data to a remote device using wireless communication.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
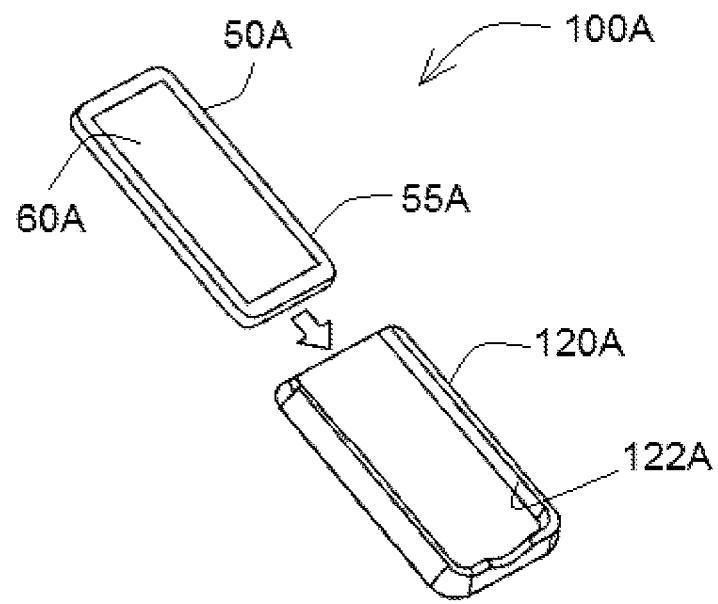
FIG. 1A illustrates a view of a sleeve and mobile computing device, according to one example.

FIG. 1A illustrates a view of system 100A including sleeve 120A and mobile computing device 50A, according to one example. Mobile computing device 50A includes user interface 60A, here shown as a touch-screen configured for displaying data and for receiving user input. Mobile computing device 50A includes housing 55A having an outer dimension that can be characterized as a length, a width, or a thickness. Mobile computing device 50A can include a cellular telephone (such as a smart-phone), a mini computer, or a tablet computer.

Sleeve 120A has inner surface 122A configured to receive housing 55A. Sleeve 120A can include a rubber molded component or a plastic component having an inner surface configured to securely couple with mobile computing device 50A and to provide physical protection to mobile computing device 50A.

Figure 1B:
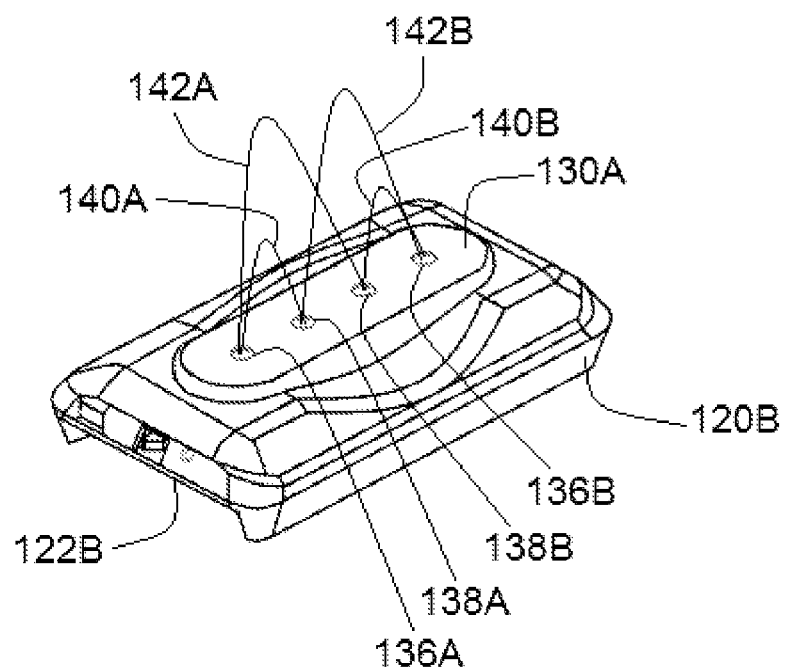
FIG. 1B illustrates a view of a sleeve, according to one example.

FIG. 1B illustrates a view of sleeve 120B, according to one example. Sleeve 120B includes inner surface 122B configured to mate with an external dimension of a mobile computing device. Sleeve 120B includes contact surface 130A. Contact surface 130A has a sensor module including emitter 138A and emitter 138B. Emitter 138A emits light that is received by detector 136A along short pathway 140A and light that is received by detector 136B along long pathway 142B. Emitter 138B emits light that is received by detector 136B along short pathway 140B and light that is received by detector 136A along long pathway 142A. Light received by detector 136A and detector 136B, using the combination of long pathway 142A, long pathway 142B, short pathway 140A, and short pathway 140B can be processed to generate a measure of regional oximetry (also called tissue oximetry). In one example, the calculation entails addition and subtraction of attenuations as detected by detector 136A and detector 136B. Detector 136A and detector 136B can include an optical transducer that provides an electrical signal corresponding to detected light.

The arrangement of optical elements (such as emitter 138A, emitter 138B, detector 136A, and detector 136B) and the number of optical elements (or transducers) can be configured for a particular purpose. In one example, contact surface 130A is arranged such that emitter 138A and emitter 138B are at opposing ends and detector 136A and detector 136B are located there between.

Figure 2:
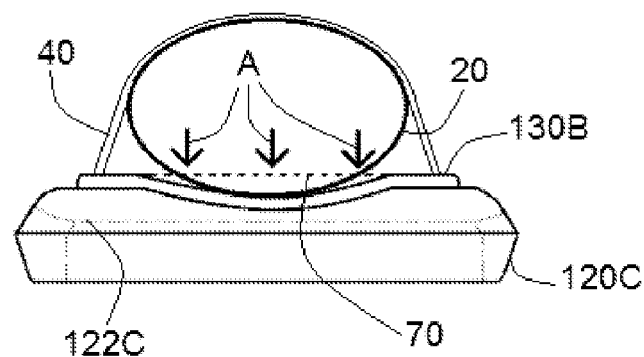
FIG. 2 illustrates a view of a sleeve with tissue, according to one example.

FIG. 2 illustrates a view of sleeve 120C with tissue 20, according to one example. Sleeve 120C includes an inner surface 122C configured to receive a mobile computing device. Sleeve 120C includes contact surface 130B. Contact surface 130B includes a sensor module configured to generate data as to tissue 20 in contact with contact surface 130B. In the example illustrated, tissue 20 is urged against contact surface 130B with sufficient force, as shown at arrows A, to deflect a complaint surface of contact surface 130B. As shown, contact surface 130B has a profile as indicated at 70 at a time before tissue 20 is urged into contact surface 130B. Strap 40 is affixed to sleeve 120C and encircles a portion of tissue 20, here shown as a section view of a limb (such as an arm or a leg). Strap 40, in one example includes a band or strap to retain tissue 20 and contact surface 130B in close proximity. In one example, contact surface 130B has a pre-formed contour that conforms to tissue 20.

Figure 3:
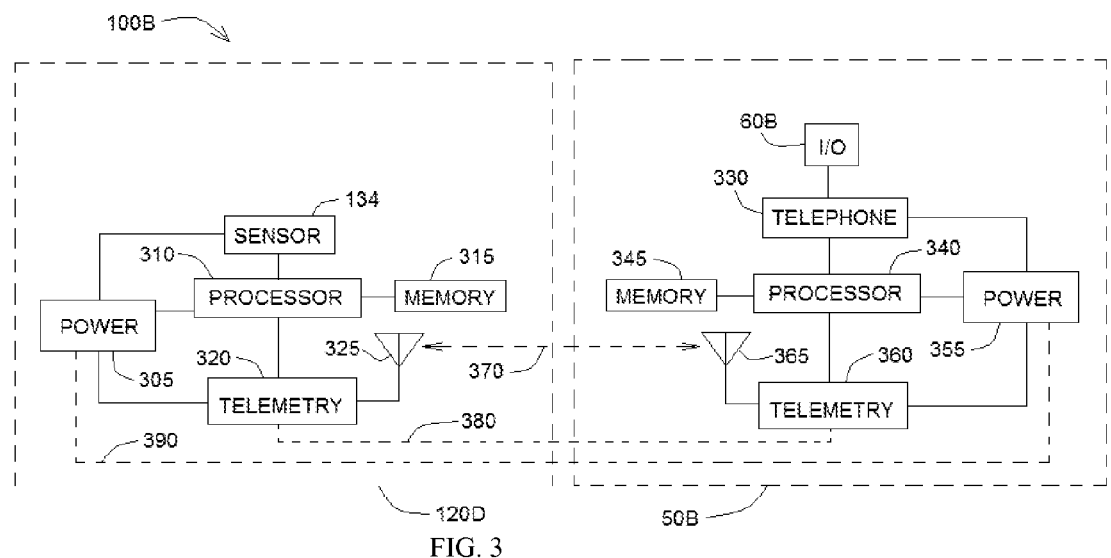
FIG. 3 illustrates a block diagram of a system, according to one example.

FIG. 3 illustrates a block diagram of system 100B, according to one example. System 100B includes sleeve 120D and mobile computing device 50B. Sleeve 120D includes sensor module 134, processor 310, memory 315, telemetry module 320, and power supply 305.

Power supply 305 can include a battery and circuitry for regulating power or for charging a battery. In one example, power 305 derives electrical energy from a wired coupling with power supply 355 of mobile computing device 50B, as shown by link 390. Power supply 305 is coupled to sensor module 134, processor 310, and telemetry module 320.

Sensor module 134 can include a one or more optical detectors (such as detector 136A or detector 136B), one or more optical emitters (such as emitter 138A and emitter 138B), a temperature sensor, a pressure sensor, or an accelerometer. In various examples, a sensor can be referred to as a transducer.

Processor 310, along with measured data from sensor module 134, can provide a variety of blood and tissue measurements. For example, a suitable algorithm and a sensor can be configured to provide data as to the following parameters or conditions:

Regional saturation (rSO2)
Hemoglobin (Hb) concentration in tissue
Tissue temperature
$SpO_2$
Total hemoglobin (tHb)
Hematocrit
Anemia
$CO_2$
COHb
MetHb
pH
Respiration
Perfusion
Apnea
Pulse wave velocity
Blood pressure
Interstitial pressure
Arterial stiffness
Intracranial Pressure
Intrauterine pressure/contractions
Glucose
Cardiac output
Bilirubin
Hydration
Hematoma
Vascular compliance
Tissue viability
Malaria
Blood cancer
Thrombocytopenia (low platelet count)
Sepsis
Thrombosis
Compartment syndrome In addition, a suitable algorithm and sensor module can provide data as to a material property of an object or as to a surface. This can include processing based on data corresponding to an optical measurement, a mechanical measurement, an acoustic measurement, or an electrical measurement. For example, data can correspond to an event counter, an event marker (time mark), a density measurement, a conductivity measurement, a concentration measurement, a color measurement, or a light level measurement.

Processor 310 can include a digital processor or an analog processor circuit. In one example, processor 310 includes a microprocessor. In the example shown, processor 310 is coupled to memory 315 and processor 310 is configured to execute instructions to implement an algorithm as described elsewhere in this document. In one example, memory 315 is configured to store data generated by sensor module 134 or configured to store calibration information for sensor module 134.

Processor 310 is coupled to telemetry module 320. In one example, telemetry module 320 includes a wired connection with a corresponding telemetry module 360 of mobile computing device 50B, as shown at link 380. In one example, telemetry module 320 communicates with telemetry module 360 by a wireless channel, as depicted by antenna 325 and antenna 365, shown at link 370. In one example, link 370 includes a radio frequency communication channel, one example of which is known commonly as Bluetooth. In other examples, link 370 includes an infrared communication channel, a near-field inductive coupling, or an ultrasonic (or acoustic) coupling.

Mobile computing device 50B includes I/O module 60B coupled to telephone module 330. I/O module 60B can include a touch-sensitive screen configured to receive user-entered data or keystrokes and configured to display visual data. Telephone module 330 can include a cellular telephone module, a text message module, or other wireless communication module. Telephone module 330 can allow data exchange with a cloud-based server or storage facility. Telephone module 330 is coupled to processor 340. Processor 340 is coupled to memory 345 and coupled to telemetry module 360. Mobile computing device 50B includes power 355 coupled to telephone module 330, processor 340, and telemetry module 360.

Figure 4:
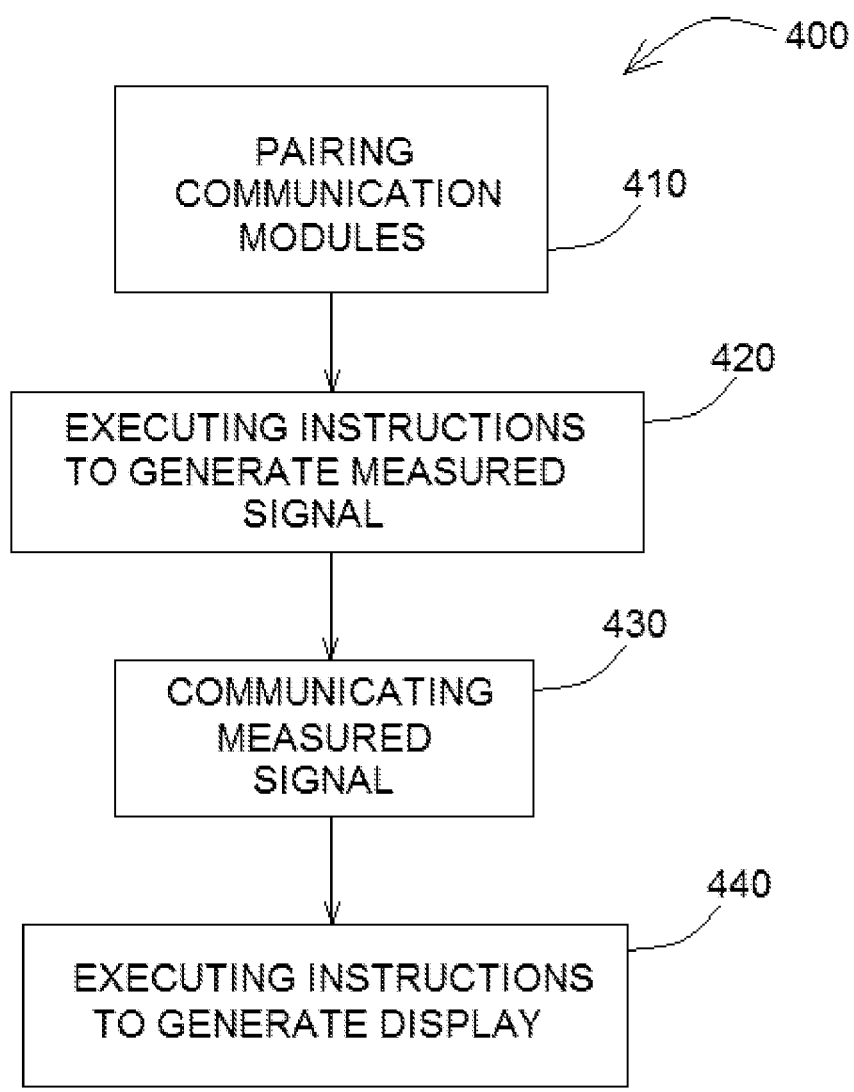
FIG. 4 illustrates a flow chart of a system, according to one example.

FIG. 4 illustrates flow chart 400 implemented by a system, according to one example. Flow chart 400 includes, at 410, pairing communication modules. In one example, this entails establishing a wireless link between telemetry module 320 (and using antenna 325) and telemetry module 360 (and using antenna 365) in a process known as pairing. Pairing can include exchanging access credentials and coordinating handshaking protocols. Some communication protocols, such as Bluetooth, are paired by executing a predetermined algorithm.

At 420, method 400 includes executing instructions to generate a measured signal using sensor module 134. This can include executing instructions (stored in memory 315) using processor 310 to implement an algorithm. The algorithm can entail operating an emitter (such as emitter 138A or emitter 138B) according to a particular protocol and receiving an output signal from a detector (such as detector 136A or detector 136B). In one example, this can include receiving a temperature signal from a temperature transducer.

At 430, method 400 includes communicating the measured signal to the mobile computing device. Communicating can include sending and receiving a wireless signal (using wireless telemetry modules) or can include communicating using a wired connection between the sleeve and the mobile computing device.

At 440, method 400 includes executing instructions using processor 340 to generate a visible display of data. The data can be displayed on user interface 60A or on I/O module 60B.

VARIOUS NOTES & EXAMPLES

Example 1 can include a system having a mobile computing device, a sleeve, a contact surface, a sensor module, and a telemetry module. The mobile computing device can include a first processor within a housing. The sleeve can include an internal surface configured to fit the housing. The contact surface can include an external surface of the sleeve. The sensor module is coupled to the contact surface and can be configured to generate an electrical signal corresponding to a measured physiological parameter associated with tissue at the contact surface. The telemetry module can be coupled to the sensor module and configured to communicate data corresponding to the electrical signal to the mobile computing device.

Example 2 can include, or can optionally be combined with the subject matter of Example 1 to optionally include wherein the mobile computing device includes a smart telephone.

Example 3 can include, or can optionally be combined with the subject matter of Example 1 to optionally include wherein the contact surface includes a compliant member, the compliant member configured to conform to a tissue contour.

Example 4 can include, or can optionally be combined with the subject matter of Example 1 to optionally include wherein the contact surface has a curved contour.

Example 5 can include, or can optionally be combined with the subject matter of Example 1 to optionally include wherein the contact surface includes a non-stick surface.

Example 6 can include, or can optionally be combined with the subject matter of Example 1 to optionally include wherein the electrical signal corresponds to regional oximetry.

Example 7 can include, or can optionally be combined with the subject matter of Example 1 to optionally include wherein the sensor module includes at least two optical detectors and wherein the electrical signal is determined by a combination of the at least two optical detectors.

Example 8 can include, or can optionally be combined with the subject matter of Example 1 to optionally include wherein the sensor module is coupled to a battery.

Example 9 can include, or can optionally be combined with the subject matter of Example 1 to optionally include a second processor coupled to the sensor module, the second processor configured to generate the data.

Example 10 can include, or can optionally be combined with the subject matter of Example 1 to optionally include wherein the telemetry module includes a wireless transceiver.

Example 11 can include, or can optionally be combined with the subject matter of Example 1 to optionally include wherein the mobile computing device is configured to execute instructions to communicate with a remote device.

Example 12 can include, or can optionally be combined with the subject matter of Example 1 to optionally include wherein the mobile computing device is configured to execute instructions to communicate with a remote device in near real-time.

Example 13 can include, or can optionally be combined with the subject matter of Example 1 to optionally include wherein the housing includes a retention strap.

Example 14 can include a device having a sleeve, a contact surface, a sensor module, and a telemetry module. The sleeve can have an internal surface configured to fit an external dimension of a mobile computing device. The contact surface is on an external surface of the sleeve. The sensor module is coupled to the contact surface and configured to generate an electrical signal corresponding to a measured physiological parameter associated with tissue at the contact surface. The telemetry module is coupled to the sensor module and configured to communicate data corresponding to the electrical signal to the mobile computing device.

Example 15 can include, or can optionally be combined with the subject matter of Example 14 to optionally include wherein the sleeve includes a rubber housing.

Example 16 can include, or can optionally be combined with the subject matter of Example 14 to optionally include wherein the electrical signal corresponds to regional oximetry.

Example 17 can include, or can optionally be combined with the subject matter of Example 14 to optionally include wherein the telemetry module includes a radio frequency transceiver.

Example 18 can include, or can optionally be combined with the subject matter of Example 14 to optionally include a battery coupled to at least one of the sensor module and the telemetry module.

Example 19 can include, or can optionally be combined with the subject matter of Example 14 to optionally include wherein the sensor module includes at least two optical detectors.

Example 20 can include a method including pairing a first communication module of a mobile computing device with a second communication module of a sleeve. The mobile computing device is configured to fit an internal surface of the sleeve. The sleeve has a sleeve processor coupled to a sleeve memory and the sleeve has a contact surface. The method includes executing instructions using the sleeve processor. The instructions are stored on the sleeve memory. The instructions are configured to generate a measured signal using an optical sensor coupled to the contact surface. The measured signal corresponds to a tissue at the contact surface. The method includes communicating the measured signal from the sleeve to the mobile computing device using the first communication module and using the second communication module. The method includes executing instructions using the device processor to generate display data for a display of the mobile computing device.

Example 21 can include, or can optionally be combined with the subject matter of Example 20 to optionally include wherein executing the instructions using the sleeve processor includes calculating a temperature using a temperature transducer.

Example 22 can include, or can optionally be combined with the subject matter of Example 20 to optionally include wherein executing the instructions using the sleeve processor includes emitting light from the optical sensor.

Example 23 can include, or can optionally be combined with the subject matter of Example 20 to optionally include wherein executing the instructions using the sleeve processor includes calculating regional oximetry.

Example 24 can include, or can optionally be combined with the subject matter of Example 20 to optionally include displaying regional oximetry data based on the display data using the display.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   a mobile computing device having a first processor within a housing;
   a sleeve having an internal surface configured to fit the housing;
   a contact surface on an external surface of the sleeve, the contact surface including a curved contour;
   a sensor module including a plurality of detectors coupled along the curved contour of the contact surface and configured to generate an electrical signal corresponding to a measured physiological parameter associated with tissue at the contact surface, wherein the curved contour is configured to arrange the plurality of detectors in contact with the tissue; and
   a telemetry module coupled to the sensor module and configured to communicate data corresponding to the electrical signal to the mobile computing device, wherein the mobile computing device is configured to determine regional oximetry based on the electrical signal.

2. The system of claim 1 wherein the mobile computing device is a smart telephone.

3. The system of claim 1 wherein the contact surface includes a compliant member, the compliant member configured to conform to a tissue contour.

4. The system of claim 1 wherein the contact surface includes a non-stick surface.

5. The system of claim 1 wherein the plurality of detectors are optical detectors, and wherein the electrical signal is determined by a combination of the optical detectors.

6. The system of claim 1 wherein the sensor module is coupled to a battery.

7. The system of claim 1 further including a second processor coupled to the sensor module, the second processor configured to generate the data.

8. The system of claim 1 wherein the telemetry module includes a wireless transceiver.

9. The system of claim 1 wherein the mobile computing device is configured to execute instructions to communicate with a remote device.

10. The system of claim 1 wherein the mobile computing device is configured to execute instructions to communicate with a remote device in near real-time.

11. The system of claim 1 wherein the sleeve includes a retention strap.

12. A device comprising:
    a sleeve having an internal surface configured to fit an external dimension of a mobile computing device;
    a contact surface on an external surface of the sleeve, the contact surface including a curved contour;
    a sensor module including a plurality of detectors coupled along the curved contour of the contact surface and configured to generate an electrical signal corresponding to a measured physiological parameter associated with tissue at the contact surface; and
    a telemetry module coupled to the sensor module and configured to communicate data corresponding to the electrical signal to the mobile computing device, wherein the electrical signal corresponds to regional oximetry.

13. The device of claim 12 wherein the sleeve includes a rubber housing.

14. The device of claim 12 wherein the telemetry module includes a radio frequency transceiver.

15. The device of claim 12 further comprising a battery coupled to at least one of the sensor module and the telemetry module.

16. The device of claim 12 wherein the plurality of detectors are optical detectors.

* * * * *